(12) United States Patent
Tabata et al.

(10) Patent No.: US 9,358,568 B2
(45) Date of Patent: Jun. 7, 2016

(54) LIQUID SPRAY APPARATUS

(75) Inventors: Makoto Tabata, Kyoto (JP); Katsuji Takahashi, Soraku-gun (JP); Yutaro Okuno, Soraku-gun (JP); Takanobu Yamauchi, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 0 days.

(21) Appl. No.: 14/342,677

(22) PCT Filed: Jul. 5, 2012

(86) PCT No.: PCT/JP2012/067181
§ 371 (c)(1),
(2), (4) Date: Mar. 4, 2014

(87) PCT Pub. No.: WO2013/042428
PCT Pub. Date: Mar. 28, 2013

(65) Prior Publication Data
US 2014/0231538 A1    Aug. 21, 2014

(30) Foreign Application Priority Data
Sep. 22, 2011   (JP) .................. 2011-207416

(51) Int. Cl.
| | | |
|---|---|---|
| *B05B 1/08* | (2006.01) | |
| *B05B 3/04* | (2006.01) | |
| *B05B 17/06* | (2006.01) | |
| *B05B 17/00* | (2006.01) | |
| *A61M 11/00* | (2006.01) | |
| *A61M 15/08* | (2006.01) | |

(52) U.S. Cl.
CPC ......... *B05B 17/0623* (2013.01); *B05B 17/0638* (2013.01); *A61M 11/005* (2013.01); *A61M 15/08* (2013.01); *A61M 2210/0612* (2013.01); *B05B 17/0646* (2013.01); *B05B 17/0676* (2013.01)

(58) Field of Classification Search
USPC ................ 239/102.1, 102.2, 590, 590.3, 575, 239/DIG. 23, 548, 552; 128/200.16
See application file for complete search history.

(56) References Cited

U.S. PATENT DOCUMENTS

| | | | |
|---|---|---|---|
| 4,912,357 A | 3/1990 | Drews et al. | |
| 6,862,224 B2 * | 3/2005 | Stubbs ..................... | 365/189.02 |

(Continued)

FOREIGN PATENT DOCUMENTS

| | | |
|---|---|---|
| JP | U-58-183270 | 12/1983 |
| JP | A-62-273069 | 11/1987 |

(Continued)

OTHER PUBLICATIONS

International Search Report issued in International Application No. PCT/JP2012/067181 mailed Sep. 25, 2012.

*Primary Examiner* — Justin Jonaitis
*Assistant Examiner* — Christopher R Dandridge
(74) *Attorney, Agent, or Firm* — Oliff PLC

(57) ABSTRACT

A liquid spray apparatus includes a liquid storage part storing a liquid, a vibratory source including a leading end, a recess being formed in a surface of the leading end, and a mesh member including a large number of micropores and arranged to abut on the surface of the leading end of the vibratory source. The liquid is supplied from the outside of the leading end to the surface and the recess of the leading end. The liquid supplied to the surface and the recess of the leading end is discharged in an atomized manner through the micropores by vibrations of the vibratory source. This liquid spray apparatus can stably spray the liquid with the vibratory source and the mesh member.

11 Claims, 13 Drawing Sheets

(56) References Cited

U.S. PATENT DOCUMENTS

| | | | |
|---|---|---|---|
| 6,863,224 B2* | 3/2005 | Terada ................ B05B 17/0623 239/102.1 |
| 7,600,511 B2* | 10/2009 | Power et al. ............ 128/200.24 |
| 8,016,209 B2* | 9/2011 | Hess ................... A01M 1/2044 239/102.1 |
| 2004/0050953 A1 | 3/2004 | Terada et al. |
| 2005/0116059 A1* | 6/2005 | Lin ........................... 239/102.2 |
| 2006/0219806 A1* | 10/2006 | Wang ................ B05B 17/0646 239/102.2 |
| 2008/0217430 A1* | 9/2008 | Feriani ............... B05B 17/0684 239/102.2 |

FOREIGN PATENT DOCUMENTS

| | | | | |
|---|---|---|---|---|
| JP | A-63-194765 | 8/1988 | | |
| JP | A-64-018465 | 1/1989 | | |
| JP | A-5-228410 | 9/1993 | | |
| JP | A-7-80368 | 3/1995 | | |
| JP | 07256170 | * | 9/1995 | ............. B05B 17/06 |
| JP | A-7-256170 | 10/1995 | | |
| JP | A-7-328503 | 12/1995 | | |
| JP | A-2001-149473 | 6/2001 | | |
| JP | A-2009-154058 | 7/2009 | | |
| WO | WO 02/28545 A1 | 4/2002 | | |

* cited by examiner

LIQUID SPRAY APPARATUS

TECHNICAL FIELD

The present invention relates to a liquid spray apparatus, and more particularly relates to a liquid spray apparatus spraying a liquid with vibratory source and a mesh member.

BACKGROUND ART

As disclosed in WO2002/028545 (PTD 1), Japanese Patent Laying-Open No. 07-256170 (PTD 2), Japanese Patent Laying-Open No. 05-228410 (PTD 3), Japanese Patent Laying-Open No. 07-328503 (PTD 4), and Japanese Patent Laying-Open No. 07-080368 (PTD 5), a liquid spray apparatus spraying a liquid with a vibratory source and a mesh member is known.

A typical liquid spray apparatus is provided with a liquid storage part storing a liquid, a mesh member having a large number of micropores and a vibratory source arranged to abut on the mesh member. The liquid is supplied from the liquid storage part to a position between the mesh member and the vibratory source. The liquid supplied to a position between the mesh member and the vibratory source is sprayed to the outside through the micropores by vibrations of the vibratory source.

CITATION LIST

Patent Document

PTD 1: WO2002/028545
PTD 2: Japanese Patent Laying-Open No. 07-256170
PTD 3: Japanese Patent Laying-Open No. 05-228410
PTD 4: Japanese Patent Laying-Open No. 07-328503
PTD 5: Japanese Patent Laying-Open No. 07-080368

SUMMARY OF INVENTION

Technical Problem

The present invention has an object to provide a liquid spray apparatus spraying a liquid with a vibratory source and a mesh member and being capable of stably spraying the liquid.

Solution to Problem

A liquid spray apparatus based on the present invention includes a liquid storage part storing a liquid, a vibratory source including a leading end, a recess being formed in a surface of the leading end, and a mesh member including a large number of micropores and arranged to abut on the surface of the leading end of the vibratory source. The liquid is supplied from the outside of the leading end to the surface and the recess of the leading end. The liquid supplied to the surface and the recess of the leading end is discharged in an atomized manner through the micropores by a vibration of the vibratory source.

Preferably, the recess is formed to extend as a groove and has a first end and a second end facing each other in a direction in which the recess extends, the second end being opposite to the first end, and the recess is provided to extend such that the first end reaches an outer circumferential surface of the leading end.

Preferably, the recess is provided to extend such that the second end reaches the outer circumferential surface of the leading end.

Preferably, the surface of the leading end of the vibratory source is circular, and a width of the recess in a direction perpendicular to the direction in which the recess extends is more than or equal to 5% and less than or equal to 50% of a diameter of the surface of the leading end.

Preferably, a depth of the recess from the surface of the leading end is more than or equal to 0.03 mm and less than or equal to 1.0 mm.

Preferably, the liquid storage part is formed such that, when the liquid spray apparatus is inclined toward the vibratory source, the liquid reaches a neighborhood of a contact part between the leading end of the vibratory source and the mesh member, and such that, when the liquid spray apparatus is held in a horizontal state, the liquid does not reach the neighborhood of the contact part, and the recess is provided to extend in the direction in which the liquid spray apparatus is inclined toward the vibratory source.

Preferably, an outer edge of the surface of the leading end has been subjected to a chamfering work having a predetermined chamfer dimension, and a depth of the recess from the surface of the leading end is smaller than the chamfer dimension.

Preferably, the chamfer dimension is larger than 0.1 mm, and the depth is 0.1 mm. Preferably, the mesh member is attached to the surface of the leading end of the vibratory source in an inclined manner at a predetermined angle.

Preferably, in a projection in which the mesh member is projected toward the leading end of the vibratory source, the mesh member is attached to the leading end of the vibratory source such that a direction in which the mesh member is inclined and the direction in which the recess extends intersect with each other.

Preferably, the mesh member is configured to be rotatable relative to the vibratory source while a state in which the mesh member and the surface of the leading end of the vibratory source abut on each other is maintained.

Preferably, the recess is provided to be depressed hemispherically in the surface of the leading end.

Preferably, the liquid storage part is formed such that, when the liquid spray apparatus is inclined toward the vibratory source, the liquid reaches a neighborhood of a contact part between the leading end of the vibratory source and the mesh member, and such that, when the liquid spray apparatus is held in a horizontal state, the liquid does not reach the neighborhood of the contact part, and the recess is positioned at a lower side in the direction of gravity on the surface of the leading end of the vibratory source in a state where the liquid spray apparatus is inclined toward the vibratory source.

Preferably, a surface roughness of a bottom of the recess is formed more roughly than the surface roughness of the surface.

Advantageous Effects of Invention

According to the present invention, a liquid spray apparatus spraying a liquid with a vibratory source and a mesh member and being capable of stably spraying the liquid can be obtained.

DESCRIPTION OF EMBODIMENTS

Figure 1:
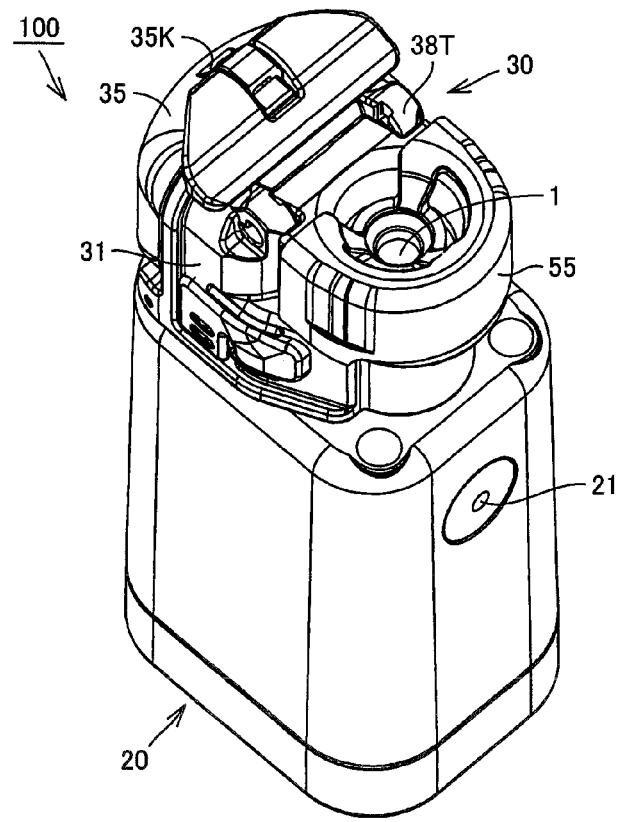
FIG. 1 is a perspective view showing an exterior structure of a liquid spray apparatus according to a first embodiment.

Hereinafter, each embodiment based on the present invention will be described with reference to the drawings. When the number, an amount or the like is mentioned in the embodiments described below, the scope of the present invention is not necessarily limited to that number, that amount or the like, unless otherwise specified. In the embodiments described below, the same or corresponding portions have the same reference characters allotted, and overlapping description may not be repeated. Combination of features in the embodiments as appropriate is originally encompassed, unless otherwise specified.

[First Embodiment]

(Liquid Spray Apparatus 100)

Referring to FIG. 1, a liquid spray apparatus 100 according to the present embodiment will be described. FIG. 1 is a perspective view showing an exterior structure of liquid spray apparatus 100. Liquid spray apparatus 100 includes a body part 20 and a bottle unit 30.

(Body Part 20)

Body part 20 has a power switch 21 on its surface. Inside body part 20, a power source (not shown), an electric circuit (not shown) and the like for driving liquid spray apparatus 100 (vibrating a horn oscillator 40 which will be described later) are provided. Bottle unit 30 is attached to body part 20 in a detachable manner.

(Bottle Unit 30)

Figure 2:
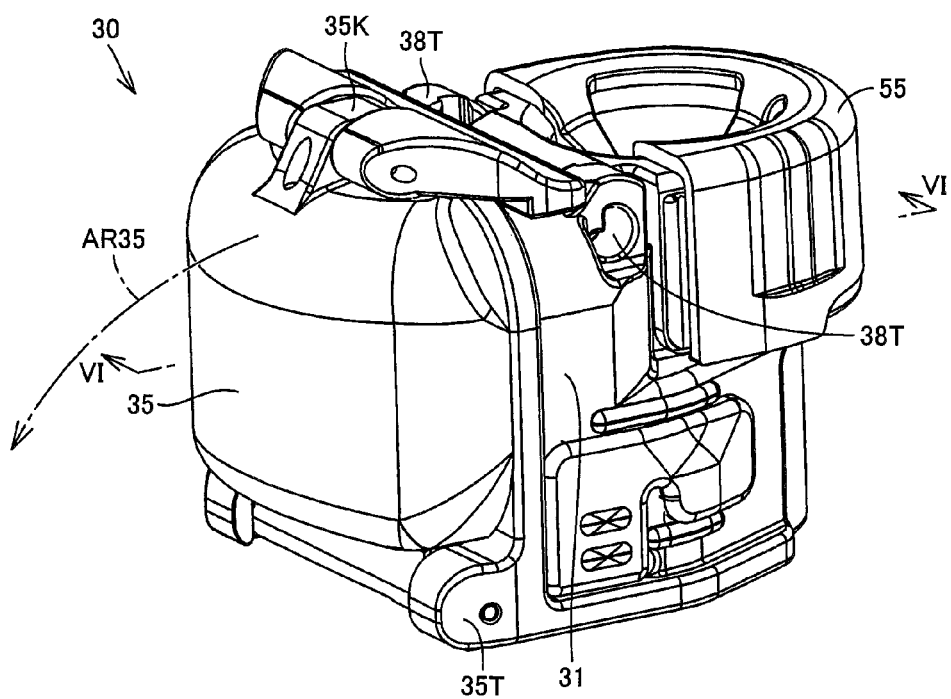
FIG. 2 is a perspective view showing a bottle unit provided for the liquid spray apparatus according to the first embodiment.
Figure 3:
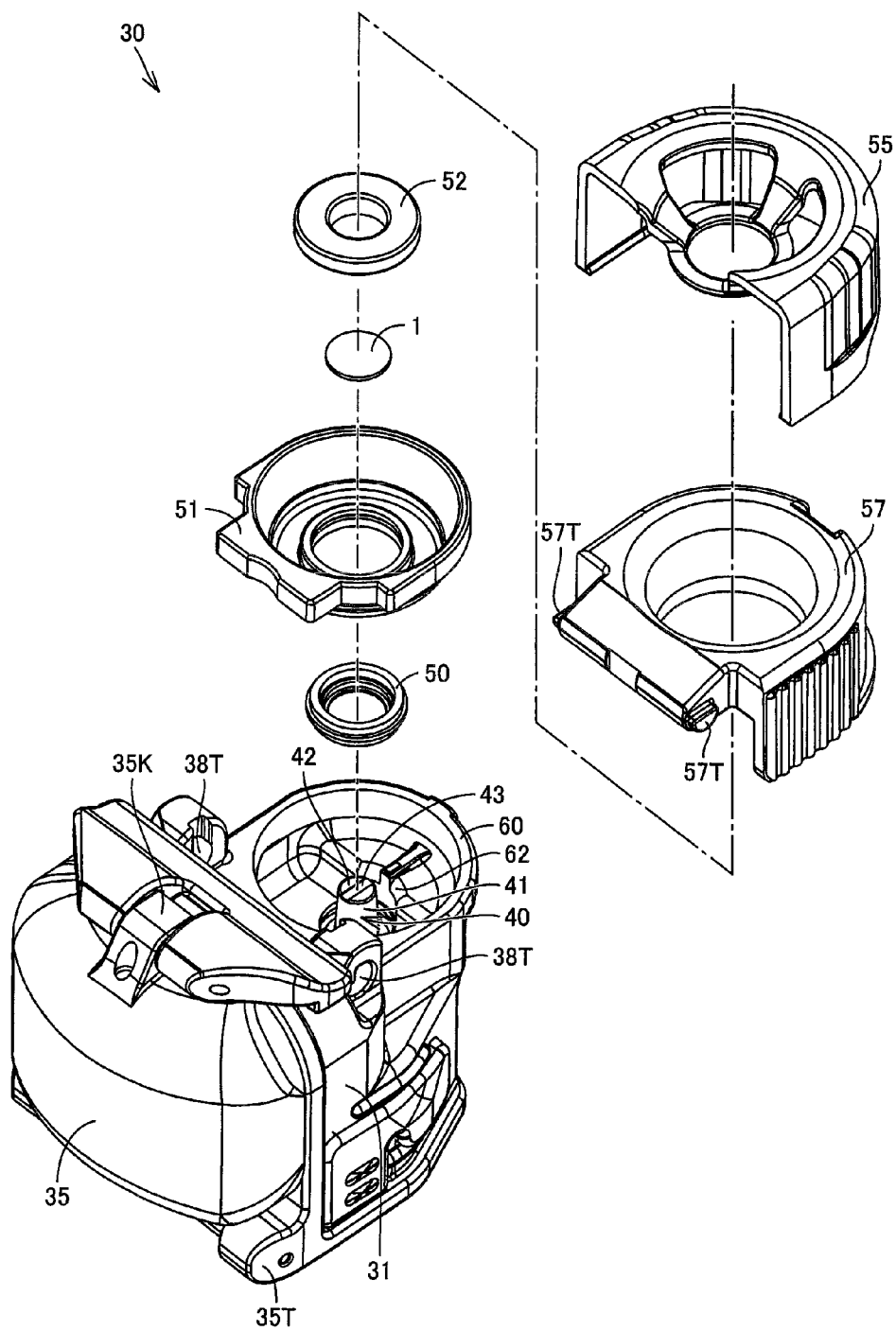
FIG. 3 is a first perspective view showing a disassembled state of the bottle unit provided for the liquid spray apparatus according to the first embodiment.
Figure 4:
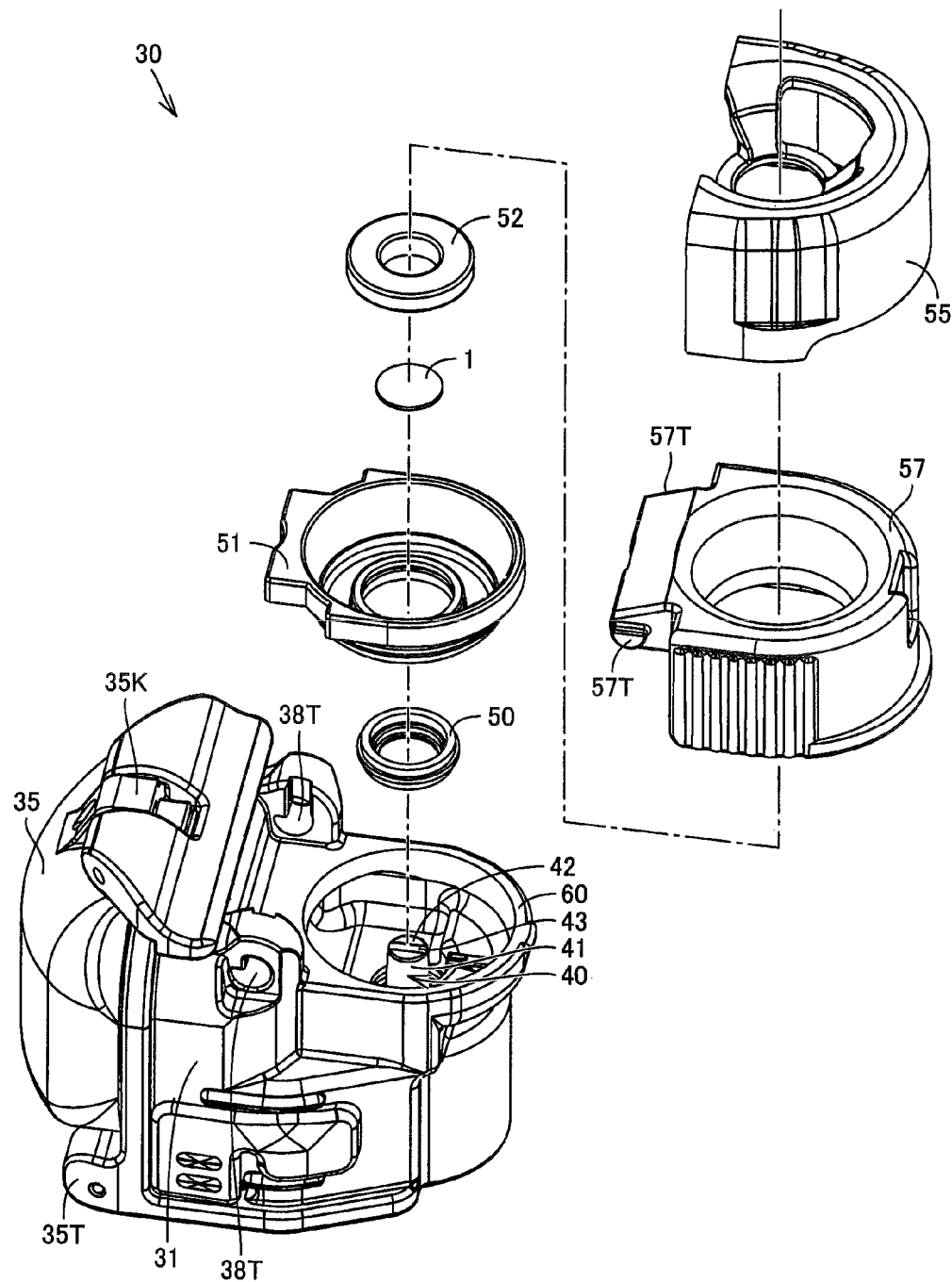
FIG. 4 is a second perspective view showing a disassembled state of the bottle unit provided for the liquid spray apparatus according to the first embodiment.
Figure 5:
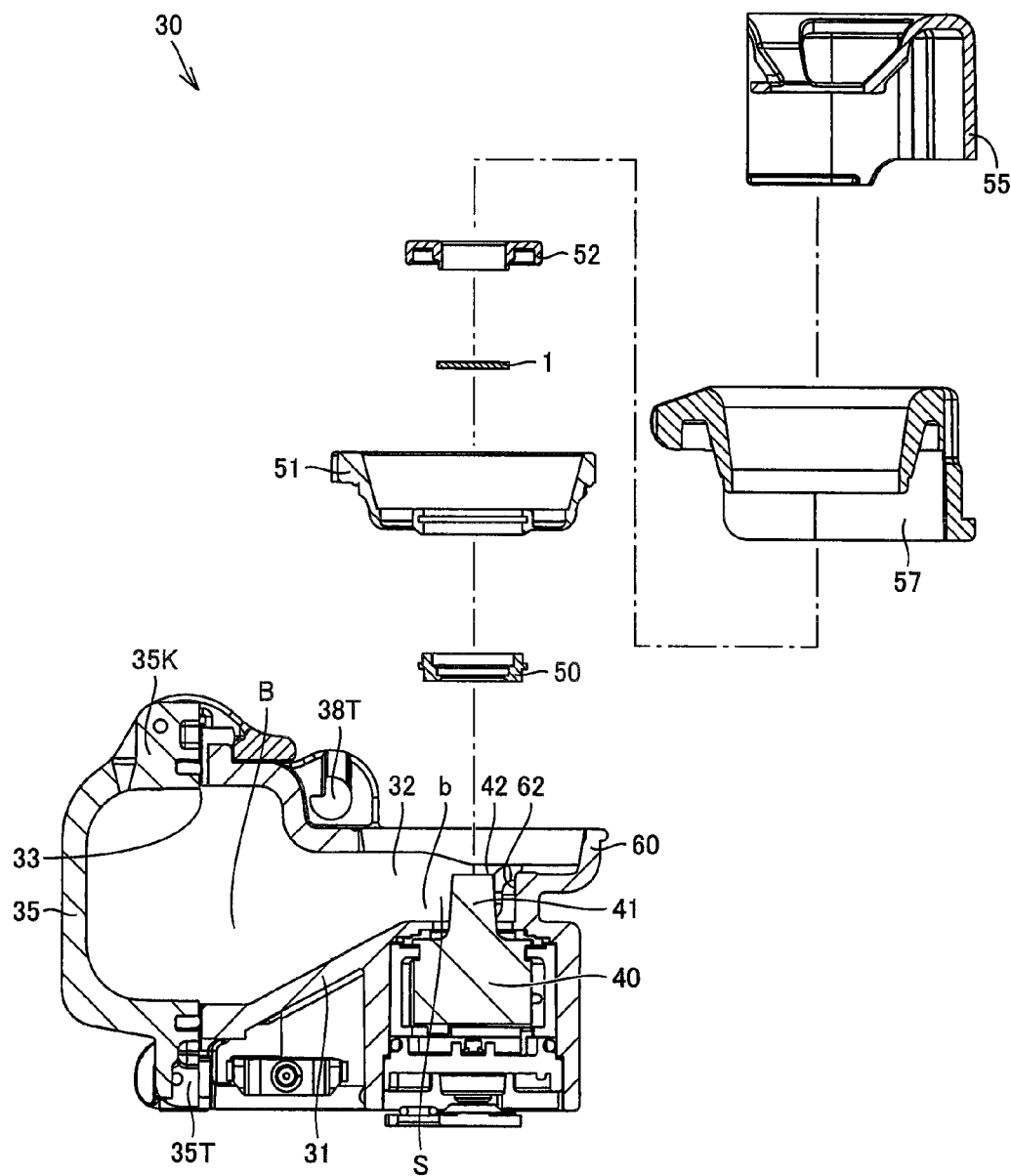
FIG. 5 is a cross sectional view showing a disassembled state of the bottle unit provided for the liquid spray apparatus according to the first embodiment.

Hereinafter, bottle unit 30 will be described in detail with reference to FIGS. 2 to 8. FIG. 2 is a perspective view showing bottle unit 30. FIG. 3 is a first perspective view showing a disassembled state of bottle unit 30. FIG. 4 is a second perspective view showing a disassembled state of bottle unit 30. FIG. 5 is a cross sectional view showing a disassembled state of bottle unit 30.

Figure 6:
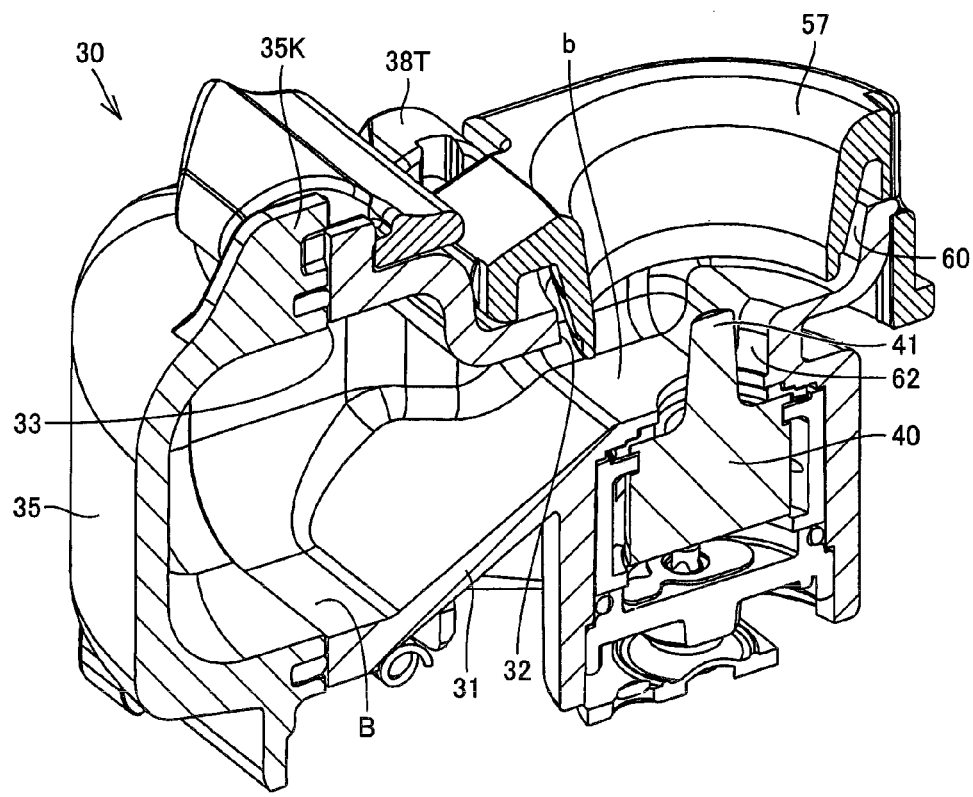
FIG. 6 is a perspective view showing a cross section taken along the line VI-VI in FIG. 2.
Figure 7:
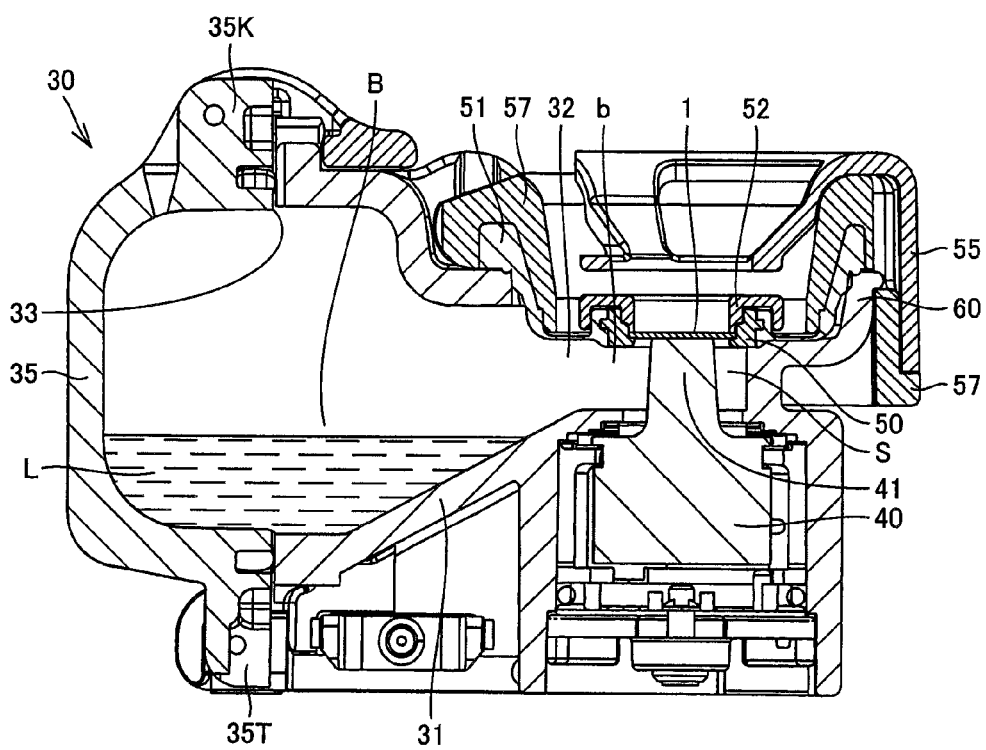
FIG. 7 is a cross sectional view corresponding to FIG. 6.
Figure 8:
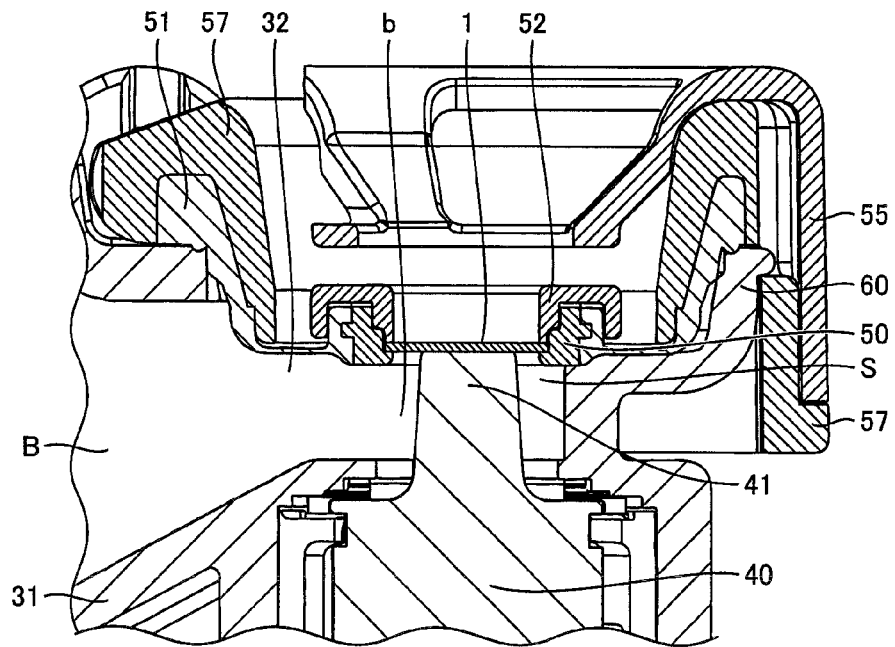
FIG. 8 is an enlarged cross sectional view of and around a mesh member in FIG. 7.

FIG. 6 is a perspective view showing a cross section taken along the line VI-VI in FIG. 2. In FIG. 6, a mesh member 1 (see FIGS. 3 to 5) (which will be described later in detail) is not shown for the sake of illustration. Similarly, in FIG. 6, mesh member 1, support members 50, 52, a sealing support packing 51, and an outer mesh cap 55 (which will also be described later in detail) are not shown. FIG. 7 is a cross sectional view corresponding to FIG. 6. FIG. 8 is an enlarged cross sectional view of and around mesh member 1 in FIG. 7.

As shown in FIGS. 2 to 5, bottle unit 30 includes mesh member 1 (see FIGS. 1 and 3 to 5), a bottle part 31 (liquid storage part) and horn oscillator 40 (vibratory source) (see FIGS. 3 to 5).

(Mesh Member 1)

Mesh member 1 has a large number of micropores (not shown). Mesh member 1 is formed of, for example, Ni—Pd (nickel-palladium) alloyed at a predetermined ratio. As will described later in detail, mesh member 1 (see FIGS. 1 and 3 to 5) is arranged to abut on a surface 42 of a leading end 41 of horn oscillator 40.

(Bottle Part 31)

Referring to FIGS. 5 to 8, the bottom of bottle part 31 is formed in an inclined manner. A liquid L (see FIG. 7), such as a medical fluid, is stored in bottle part 31.

Bottle part 31 is provided with a liquid inlet 33 located opposite to horn oscillator 40 and a leading end opening 32 gradually tapering toward horn oscillator 40. A cap 35 is attached so as to close liquid inlet 33. Cap 35 is pivotally supported by a support part 35T in the direction of an arrow AR35 (see FIG. 2).

With cap 35 attached to bottle part 31, liquid inlet 33 of bottle part 31 is closed. The state in which cap 35 closes liquid inlet 33 is held by a fixing part 35K provided on the upper part of cap 35.

Leading end opening 32 of bottle part 31 is opposed to leading end 41 of horn oscillator 40. As will be described later in detail, liquid L stored in bottle part 31 is supplied from the outside of leading end 41 of horn oscillator 40 to surface 42 of leading end 41.

Here, bottle part 31 bottle part 31 is formed such that liquid L does not reach the neighborhood of a contact part (atomizing part) between the surface (surface 42 in FIG. 3 etc.) of leading end 41 of horn oscillator 40 and mesh member 1 when liquid spray apparatus 100 (see FIG. 1) is held in a horizontal state (a horizontal state shown in FIG. 7). On the other hand, bottle part 31 is formed such that liquid L reaches the neighborhood of the contact part (atomizing part) of the surface (surface 42 in FIG. 3 etc.) of leading end 41 of horn oscillator 40 and mesh member 1 in the spray state (an inclined state shown in FIG. 9) in which liquid spray apparatus 100 (see FIG. 1) is inclined toward horn oscillator 40.

Specifically, in the present embodiment, bottle part 31 has a larger capacity section B and a smaller capacity section b communicating with this larger capacity section B via leading end opening 32 and facing leading end 41 of horn oscillator 40. Smaller capacity section b leaves an annular space S (see FIG. 5) between inner wall 62 (see FIG. 6) of an opening 60 of bottle unit 30 through which an atomized medical fluid is sprayed and leading end 41 of horn oscillator 40.

Smaller capacity section b is formed such that this liquid L (liquid LL in FIG. 9) comes into contact with the neighborhood of the atomizing part in the state where liquid L has reached space S in smaller capacity section b (see FIG. 5). Smaller capacity section b is formed such that liquid LL reaches the atomizing part even when liquid LL (see FIG. 9) is supplied into space S by a slight quantity. With this structure, in the spray state (the inclined state shown in FIG. 9) in which liquid spray apparatus 100 (see FIG. 1) is inclined toward horn oscillator 40, Liquid LL (see FIG. 9) flowing from larger capacity section B of bottle part 31 into smaller capacity section b adheres to the circumference and surface 42 of leading end 41 of horn oscillator 40.

The spacing between inner wall 62 and leading end 41 of horn oscillator 40 forming space S may be set such that liquid LL in smaller capacity section b is supplied to the neighborhood of the atomizing part by the surface tension between mesh member 1 and leading end 41 when liquid L in larger capacity section B is reduced to a slight quantity just before running out.

Bottle part 31 is formed such that liquid L in larger capacity section B and liquid LL in smaller capacity section b are separated from each other when liquid L in larger capacity section B falls below a certain quantity in a temporarily placed orientation (e.g., the horizontal state shown in FIG. 7) other than the time of normal spraying (the inclined state in FIG. 9). Smaller capacity section b is at a position higher than larger capacity section B. Therefore, in the case where liquid L does not completely fill up larger capacity section B and the liquid surface is positioned below leading end opening 32, only a small quantity of liquid LL in smaller capacity section b remains around leading end 41 of horn oscillator 40, and other liquid L is stored in larger capacity section B.

It is noted that, in the state where cap 35 is attached to bottle part 31 and outer mesh cap 55 and an inner mesh cap 57 which will be described later are attached to opening 60, the inside of bottle part 31 is kept liquid-tightly except an outer air introduction hole (not shown) formed in cap 35.

(Horn Oscillator 40)

Referring to FIGS. 5 and 6, as described above, horn oscillator 40 is disposed to be opposed to leading end opening 32 of bottle part 31. Horn oscillator 40 is located under opening 60 provided in bottle unit 30. Above horn oscillator 40, outer mesh cap 55 and inner mesh cap 57 which will be described later are attached to opening 60 in a detachable manner.

(Support Members 50 and 52)

Referring to FIGS. 7 and 8 (and FIGS. 3 to 5), support members 50 and 52 are configured such that they can be fitted together with mesh member 1 interposed therebetween. Mesh member 1 is held between support members 50 and 52 fitted to each other above leading end 41 of horn oscillator 40. Support members 50 and 52 hold mesh member 1 therebetween, and fix mesh member 1 such that mesh member 1 abuts on surface 42 of horn oscillator 40.

(Sealing Support Packing 51, Inner Mesh Cap 57 and Outer Mesh Cap 55)

Support members 50 and 52 fitted to each other are attached to the inner circumference of sealing support packing 51 formed annularly. Support members 50 and 52 fitted to each other are attached to inner mesh cap 57 by means of sealing support packing 51. The outer circumference of sealing support packing 51 is fitted into inner mesh cap 57. An air gap between support members 50, 52 and inner mesh cap 57 is sealed by sealing support packing 51.

Inner mesh cap 57 is attached around opening 60 so as to cover opening 60 provided in bottle unit 30. Inner mesh cap 57 has support parts 57T pivotally supported by support parts 38T provided on the bottle part 31 side. Outer mesh cap 55 is provided so as to externally cover inner mesh cap 57.

With inner mesh cap 57 attached around opening 60, an air gap left between inner mesh cap 57 and opening 60 is sealed by sealing support packing 51. This sealing prevents liquid L and liquid LL stored in bottle part 31 from leaking out of bottle part 31. Accordingly, even when liquid spray apparatus 100 is inclined, liquid L and liquid LL in bottle part 31 do not leak to the outside.

Here, it is necessary to keep mesh member 1 in contact with surface 42 of leading end 41 of horn oscillator 40 by proper force. The contact pressure of mesh member 1 against surface 42 may vary because of dimensional variations in each component occurring in manufacturing, variations occurring when assembling the respective components, or the like.

In liquid spray apparatus 100 according to the present embodiment, support members 50, 52 holding mesh member 1 therebetween are supported by sealing support packing 51. Since mesh member 1 comes into contact with surface 42 of leading end 41 of horn oscillator 40 with sealing support packing 51 interposed therebetween, the above-mentioned variations are absorbed by elasticity of sealing support packing 51 itself. Therefore, in liquid spray apparatus 100, stable positional relationship is maintained between mesh member 1 and surface 42 of leading end 41.

As above-described, support parts 57T of inner mesh cap 57 are pivotally supported by support parts 38T provided on the bottle part 31 side. With this structure, inner mesh cap 57 is attached to opening 60 in a detachable manner with mesh member 1, support members 50, 52 and sealing support packing 51 integrally attached to the inside of inner mesh cap 57.

Since mesh member 1 is attached to inner mesh cap 57, mesh member 1 can be washed easily by removing inner mesh cap 57 from opening 60 (rotating inner mesh cap 57).

(Operation of Liquid Spray Apparatus 100)

In the state where liquid spray apparatus 100 with bottle unit 30 attached to body part 20 (see FIG. 1) is placed on a desk or the like, bottle unit 30 is oriented horizontally, and liquid L in bottle part 31 collects at the bottom of bottle part 31, as shown in FIG. 7.

Figure 9:
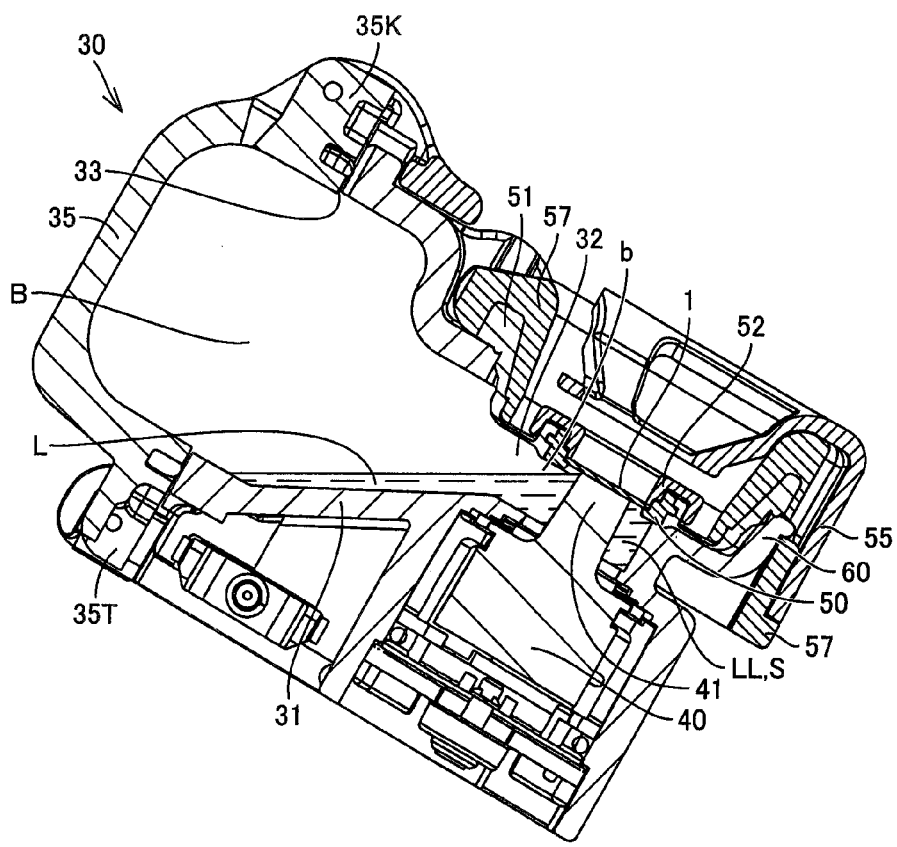
FIG. 9 is a cross sectional view showing a state of the bottle unit used for the liquid spray apparatus according to the first embodiment at the time of spraying.
Figure 10:
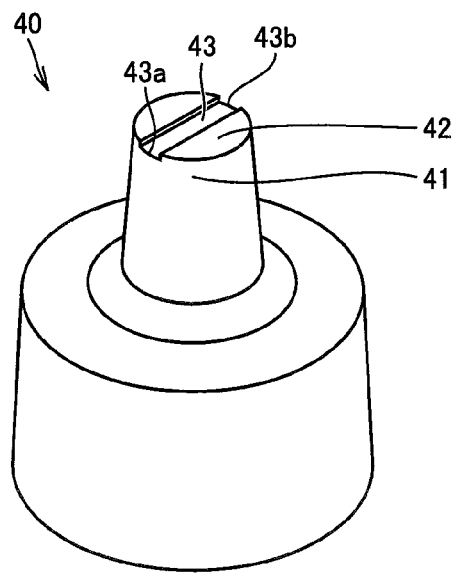
FIG. 10 is a perspective view showing a horn oscillator used for the liquid spray apparatus according to the first embodiment.
Figure 11:
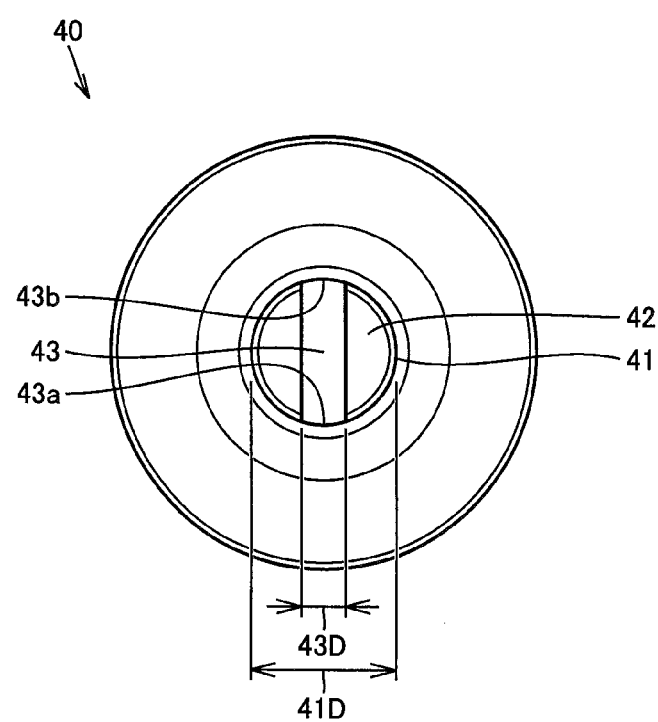
FIG. 11 is a plan view showing the horn oscillator used for the liquid spray apparatus according to the first embodiment.
Figure 12:
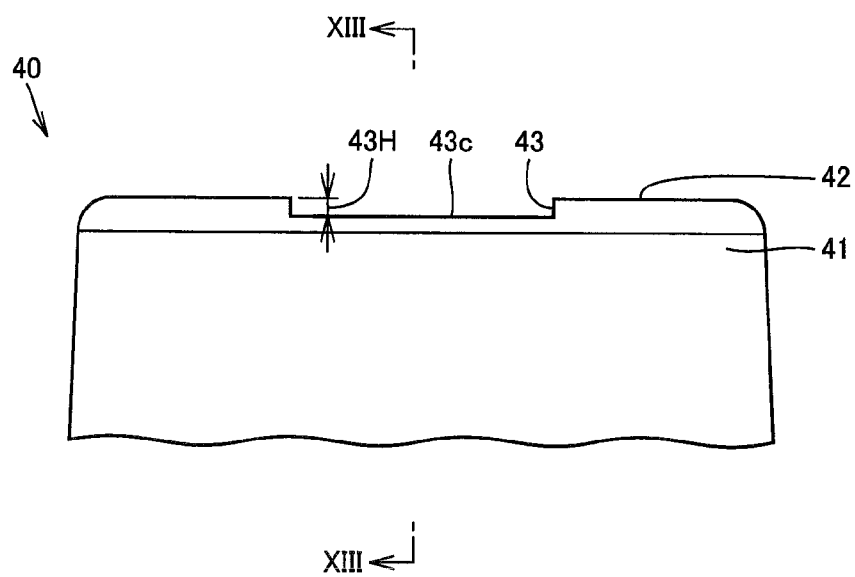
FIG. 12 is a side view of and around a surface of a leading end of the horn oscillator used for the liquid spray apparatus according to the first embodiment.
Figure 13:
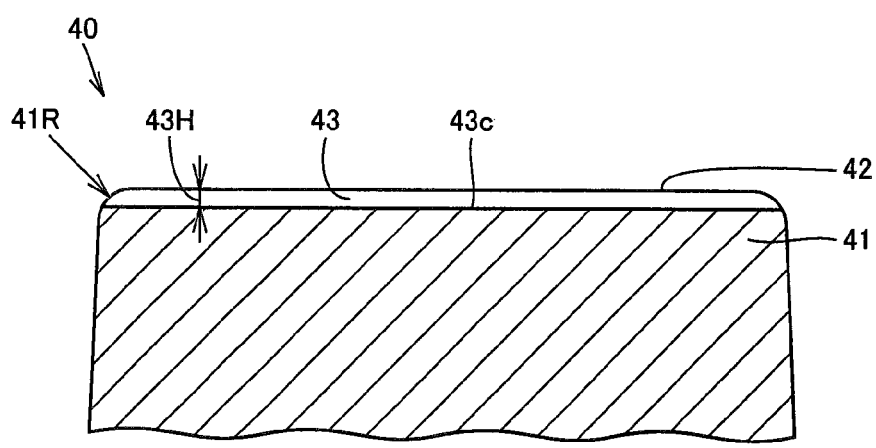
FIG. 13 is a cross sectional view taken along the line XIII-XIII in FIG. 12.

When liquid spray apparatus 100 is held in hand and inclined toward horn oscillator 40, bottle unit 30 is inclined as shown in FIG. 9, so that liquid L in larger capacity section B of bottle part 31 flows into space S in smaller capacity section b via leading end opening 32. Liquid LL in space S reaches the neighborhood of the contact part between surface 42 of leading end 41 and mesh member 1 from the outside of leading end 41 of horn oscillator 40.

If power switch 21 (see FIG. 1) of body part 20 is pressed in this state, horn oscillator 40 ultrasonically vibrates. Liquid LL is discharged through the micropores of mesh member 1 by the ultrasonic vibrations of mesh member 1 and surface 42 of leading end 41 of horn oscillator 40, so that atomized liquid LL is sprayed through opening 60 (see FIGS. 3 to 5). In liquid spray apparatus 100 according to the present embodiment, a recess 43 (which will be described later in detail) is formed in surface 42 of leading end 41. Therefore, during spraying, liquid L (liquid LL) is stably supplied by a small quantity from smaller capacity section b to mesh member 1.

Even when liquid L in larger capacity section B of bottle part 31 is reduced to a slight quantity (see FIG. 9), liquid LL in smaller capacity section b can be raised to the neighborhood of the atomizing part by the surface tension between leading end 41 of horn oscillator 40 and inner wall 62 (see FIG. 6) as described above to be supplied further to mesh member 1 by vibrations of horn oscillator 40.

On the other hand, in the state other than the time of normal use (e.g., the case of temporarily stopping a spray operation or placing liquid spray apparatus 100 on a desk etc.), liquid L slightly adheres to inner wall 62 of smaller capacity section b and most part of liquid L is stored in larger capacity section B, except the case where capacity section B of bottle part 31 is nearly full of liquid L. Liquid L is prevented from being consumed uselessly even when power switch 21 is left on. In combination with an auto power off function for the time of runout of liquid L, the battery can also be prevented from being consumed uselessly.

Moreover, liquid L is not supplied to the contact part between surface 42 of leading end 41 of horn oscillator 40 and mesh member 1 except the time of normal spraying (when in the horizontal state shown in FIG. 7). Since liquid L is not supplied to mesh member 1, oozing and leakage of liquid L will not take place. Liquids L and LL in bottle part 31 will not leak to the outside.

(Horn Oscillator 40)

Here, referring to FIGS. 10 to 14, horn oscillator 40 used for liquid spray apparatus 100 (see FIG. 1) according to the present embodiment will be described in detail. FIG. 10 is a perspective view showing horn oscillator 40 according to the present embodiment. FIG. 11 is a plan view showing horn oscillator 40. FIG. 12 is a side view of and around surface 42 of leading end 41 of horn oscillator 40. FIG. 13 is a cross sectional view taken along the line XIII-XIII in FIG. 12. FIG. 14 is a cross sectional view showing a state of horn oscillator 40 at the time of spraying.

As shown in FIGS. 10 to 14, surface 42 of leading end 41 of horn oscillator 40 is provided with recess 43 extending like a groove in a substantially diametrical direction of surface 42. Horn oscillator 40 may be fixed with the phase in a rotation direction positioned such that recess 43 extends in the direction in which liquid spray apparatus 100 is inclined toward horn oscillator 40.

Recess 43 according to the present embodiment has a first end 43*a* and a second end 43*b*. First end 43*a* and second end 43*b*are opposed to each in the direction in which recess 43 extends. Second end 43*b* is located at the opposite side of first end 43*a*. Recess 43 according to the present embodiment is formed to extend such that first end 43*a* and second end 43*b* both reach the outer circumferential surface of leading end 41.

As shown in FIG. 11, surface 42 of leading end 41 of horn oscillator 40 according to the present embodiment has a circular shape. Surface 42 has a diameter of about 3.5 mm, for example. A width 43D of recess 43 in the direction (in the horizontal direction on the drawing sheet of FIG. 11) perpendicular to the direction in which recess 43 extends (the vertical direction on the drawing sheet of FIG. 11) is about 1.0 mm, for example. Width 43D is preferably more than or equal to 5% and less than or equal to 50% of the diameter of surface 42. If width 43D of recess 43 is excessively large (if surface 42 is excessively reduced in area), an unstable spray state may be brought about and favorable spraying may not be achieved. On the other hand, if width 43D of recess 43 is excessively small, the essential effect of recess 43 may not be obtained. Therefore, width 43D is preferably more than or equal to 5% and less than or equal to 50% of the diameter of surface 42.

Referring to FIGS. 12 and 13, recess 43 has a depth 43H from surface 42 of about 0.1 mm, for example. Depth 43H is preferably more than or equal to 0.03 mm and less than or equal to 1.0 mm. If the value of depth 43H does not fall within this range, an unstable spray state may be brought about and favorable spraying may not be achieved. If the width of recess 43 is narrow and depth 43H is excessively deep, it may not be desirable in terms of cleaning. On the other hand, if depth 43H of recess 43 is excessively shallow, the essential effect of recess 43 may not be obtained. Therefore, depth 43H is preferably more than or equal to 0.03 mm and less than or equal to 1.0 mm. The surface of a bottom 43*c* of recess 43 is formed more roughly than the surface of surface 42 (surface roughness of bottom 43*c*>surface roughness of surface 42).

Referring to FIG. 13, the outer edge of surface 42 of leading end 41 of horn oscillator 40 has been subjected to an R chamfering work having a predetermined processing radius 41R (chamfer dimension). Processing radius 41R is larger than 0.1 mm (R0.1 mm), and is about 0.2 mm, for example.

Depth 43H of recess 43 from surface 42 of leading end 41 is preferably provided to be smaller than processing radius 41R. In the case where recess 43 is formed by cutting with an end mill or the like, burrs may be formed at first end 43*a* or second end 43*b* of recess 43. In the case where the outer edge of surface 42 is subjected to the R chamfering work after the formation of recess 43, burrs can be removed because depth 43H of recess 43 from surface 42 of leading end 41 is formed smaller than processing radius 41R.

The outer edge of surface 42 of leading end 41 of horn oscillator 40 is not limited to the R chamfering work, but may be subjected to a C chamfering work having a predetermined chamfer dimension. Also in this case, the chamfer dimension is larger than 0.1 mm (C0.1 mm), and is preferably about 0.2 mm, for example. With this structure, the above-mentioned burrs can also be removed.

Referring to FIG. 14, by providing recess 43 in surface 42 of leading end 41 of horn oscillator 40, a space corresponding to the shape of recess 43 is left between mesh member 1 and surface 42. As described above, liquid L (liquid LL) is supplied from bottle part 31 toward horn oscillator 40. Liquid L (liquid LL) is supplied from the outside of leading end 41 of horn oscillator 40 to surface 42 of leading end 41.

Furthermore, liquid L (liquid LL) is supplied from the outside of leading end 41 to a position between surface 42 of leading end 41 in horn oscillator 40 and mesh member 1. At this time, liquid L (liquid LL) can also reach the lower surface side of mesh member 1, wile flowing from the outside of leading end 41 into the space created by recess 43 (see an arrow AR in FIG. 14).

Liquid L collects in recess 43. The quantity of liquid L (liquid LL) supplied to mesh member 1 is locally increased between mesh member 1 and surface 42 by providing recess 43 in surface 42. Liquid L (liquid LL) can be stably supplied to mesh member 1.

Power switch 21 of body part 20 (see FIG. 1) is pressed in the state where liquid L (liquid LL) is stably supplied to mesh member 1. Horn oscillator 40 ultrasonically vibrates, and liquid LL in smaller capacity section b is supplied to mesh member 1 by the ultrasonic vibrations of mesh member 1 and surface 42 of leading end 41 of horn oscillator 40. Liquid LL is discharged as droplets from the micropores of mesh member 1, and is sprayed via opening 60. During spraying, liquid L (liquid LL) is reliably supplied by a small quantity to mesh member 1 via recess 43.

Liquid L (liquid LL) is stably supplied to mesh member 1 without interruption. Therefore, liquid spray apparatus 100 according to the present embodiment can stably spray liquid L (liquid LL).

Figure 14:
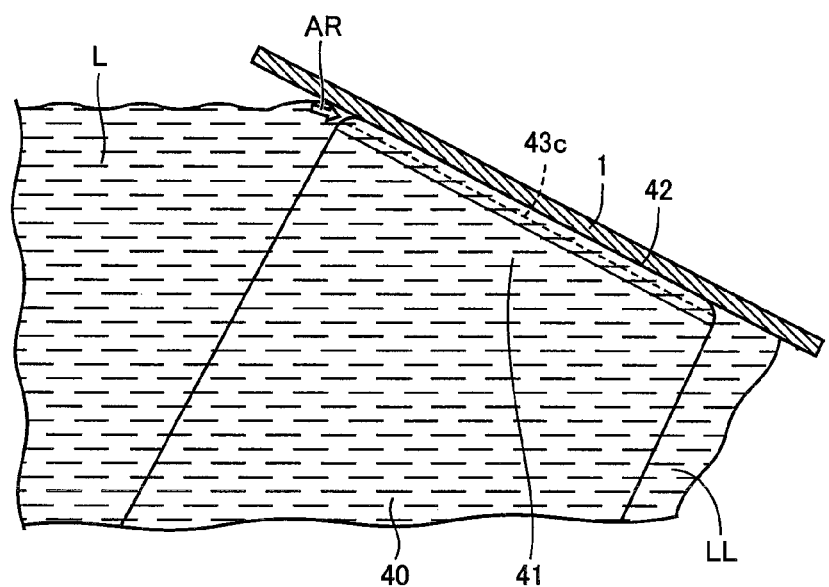
FIG. 14 is a cross sectional view showing a state of the horn oscillator used for the liquid spray apparatus according to the first embodiment at the time of spraying.

Moreover, when recess 43 of horn oscillator 40 extends in the direction in which liquid spray apparatus 100 is inclined toward horn oscillator 40 (the state shown in FIG. 14), liquid L (liquid LL) can be more stably supplied to mesh member 1 without interruption.

In the case where recess 43 is provided at the center of surface 42, the vibrational energy of horn oscillator 40 concentrates on the center of surface 42. Therefore, a continuous spray state can be achieved more stably.

Recess 43 according to the present embodiment is provided to extend such that first end 43a and second end 43b both reach the outer circumferential surface of leading end 41. Since the both ends of recess 43 are open, liquid L is restrained from being supplied excessively (overflown) to mesh member 1.

[Second Embodiment]

Figure 15:
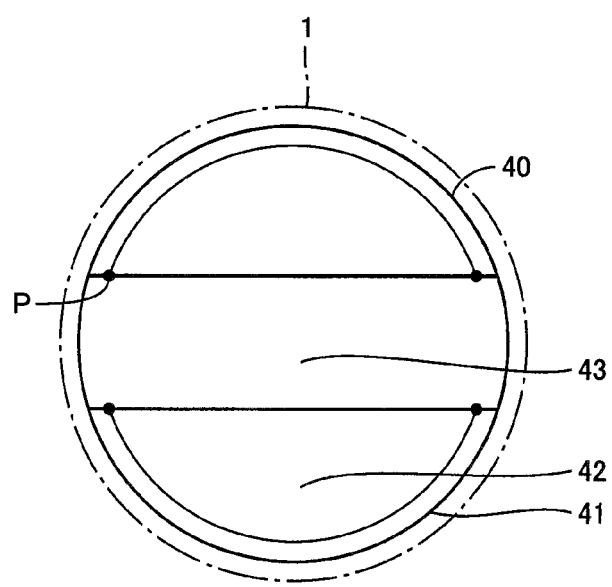
FIG. 15 is a plan view showing a horn oscillator used for a liquid spray apparatus of a comparative example of a second embodiment.
Figure 16:
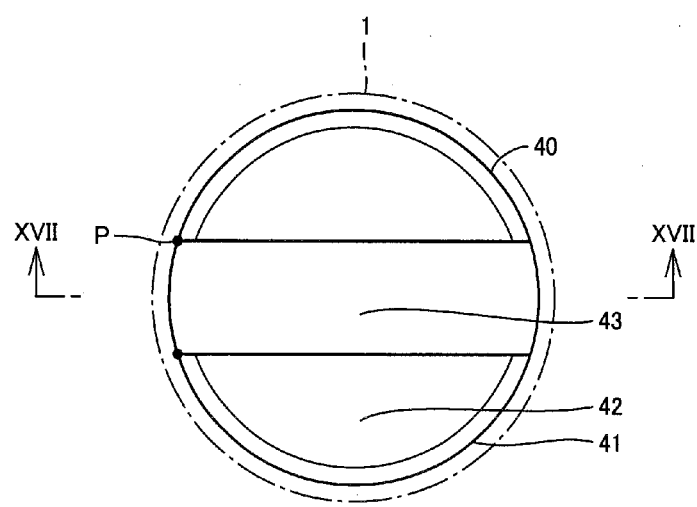
FIG. 16 is a plan view showing a horn oscillator used for a liquid spray apparatus according to the second embodiment.
Figure 17:
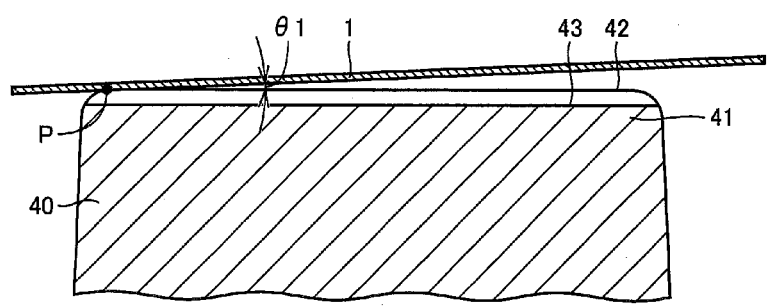
FIG. 17 is a cross sectional view taken along the line XVII-XVII in FIG. 16.

Referring to FIGS. 15 to 17, a liquid spray apparatus according to the present embodiment will be described. Here, a difference from liquid spray apparatus 100 (see FIG. 1) according to the above-described first embodiment will be described.

As shown in FIG. 15, by providing recess 43 in surface 42, four corners P are formed in surface 42 of horn oscillator 40. Even if the outer edge of surface 42 of leading end 41 is not subjected to the R chamfering work, four corners P are formed similarly.

Suppose that mesh member 1 abuts on surface 42 in parallel to surface 42 of leading end 41 of horn oscillator 40. In this case, mesh member 1 receives local stress from four corners P by ultrasonic vibrations with surface 42 of leading end 41, so that portions of mesh member 1 in contact with corners P are likely to be damaged.

FIG. 16 is a plan view showing horn oscillator 40 used for the liquid spray apparatus according to the present embodiment. FIG. 17 is a cross sectional view taken along the line XVII-XVII in FIG. 16.

Referring to FIGS. 16 and 17, in the present embodiment, mesh member 1 is attached in an inclined manner at a predetermined angle θ1 (see FIG. 17) to surface 42 of leading end 41 of horn oscillator 40. With this structure, the number of portions of mesh member 1 in contact with corners P is reduced to two. Portions of mesh member 1 to be damaged are reduced, and the likelihood that mesh member 1 will be damaged can be reduced.

[Third Embodiment]

Figure 18:
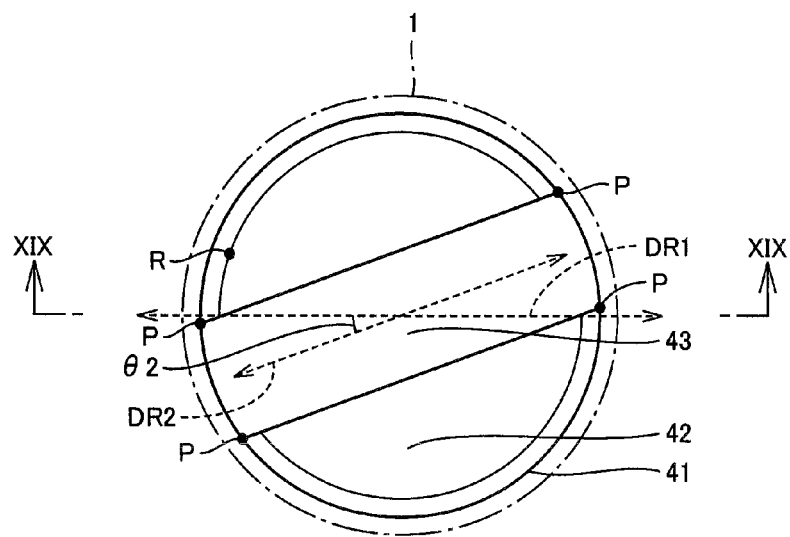
FIG. 18 is a plan view showing a horn oscillator used for a liquid spray apparatus according to a third embodiment.
Figure 19:
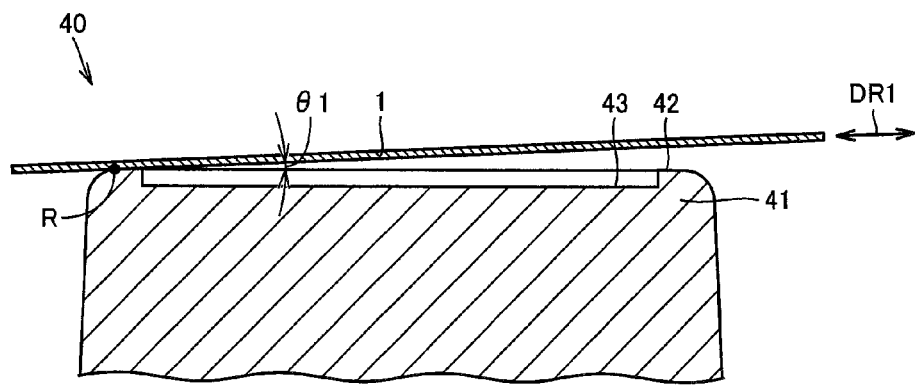
FIG. 19 is a cross sectional view taken along the XIX-XIX line in FIG. 18.

Referring to FIGS. 18 and 19, a liquid spray apparatus according to the present embodiment will be described. Here, a difference from the liquid spray apparatus (FIGS. 16, 17) according to above-described second embodiment will be described.

Referring to FIGS. 18 and 19, mesh member 1 is attached to surface 42 of leading end 41 of horn oscillator 40 in an inclined manner at predetermined angle θ1 (see FIG. 19). In other words, mesh member 1 is attached in an inclined manner in a direction of an arrow DR1.

As shown in FIG. 18, in the present embodiment, in a projection in which mesh member 1 is projected on the leading end 41 side of horn oscillator 40, mesh member 1 is attached to surface 42 of leading end 41 of horn oscillator 40 such that the direction in which mesh member 1 is inclined (the direction of arrow DR1) and the direction in which recess 43 extends (the direction of arrow DR2) intersect with each other.

That is, in the above-mentioned projection, a predetermined angle θ2 is provided between the direction in which mesh member 1 is inclined (the direction of arrow DR1) and the direction in which recess 43 extends (the direction of arrow DR2).

With this structure, mesh member 1 does not contact corners P but comes into contact with surface 42 of leading end 41 at edges R except corners P. The likelihood that mesh member 1 will be damaged can further be reduced.

[Fourth Embodiment]

Figure 20:
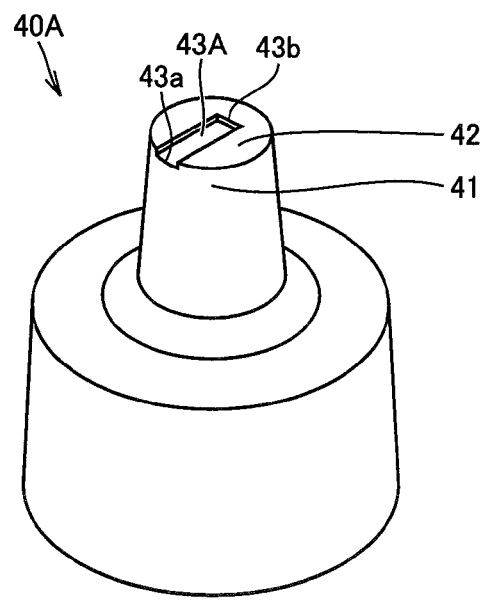
FIG. 20 is a perspective view showing a horn oscillator used for a liquid spray apparatus according to a fourth embodiment.

Referring to FIG. 20, a liquid spray apparatus according to the present embodiment will be described. A horn oscillator 40A is used in the liquid spray apparatus according to the present embodiment. In horn oscillator 40A, a recess 43A is provided in surface 42 of leading end 41.

Recess 43A according to the present embodiment is formed such that first end 43a reaches the outer circumferential surface of leading end 41. Second end 43b does not reach the outer circumferential surface of leading end 41. When recess 43A is not provided to cross surface 42 as in the present embodiment, liquid L supplied onto surface 42 can be stored in recess 43A.

Because liquid L is stored in recess 43A, liquid L can be stably supplied to mesh member 1 without interruption. As a result, liquid L can be sprayed stably.

By applying the structure of the above-described second or third embodiment to the structure of the fourth embodiment, the likelihood that mesh member 1 will be damaged can be reduced.

[Fifth Embodiment]

Figure 21:
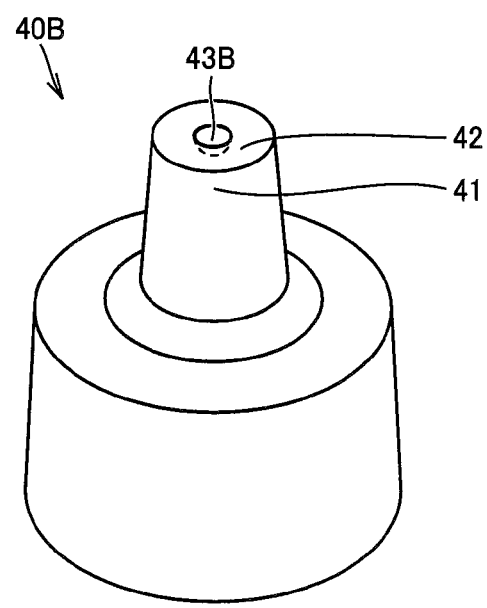
FIG. 21 is a perspective view showing a horn oscillator used for a liquid spray apparatus according to a fifth embodiment.

Referring to FIG. 21, a liquid spray apparatus according to the present embodiment will be described. A horn oscillator 40B is used in the liquid spray apparatus according to the present embodiment. In horn oscillator 40B, a recess 43B is provided in surface 42 of leading end 41. Recess 43B is provided to be depressed hemispherically in surface 42 of leading end 41. In this case, liquid L supplied on surface 42 can also be stored in recess 43B, similarly to the above-described fourth embodiment.

Because liquid L is stored in recess 43B, liquid L can be supplied stably to mesh member 1 without interruption. As a result, liquid L can be sprayed stably.

[Variation of Fifth Embodiment]

Figure 22:
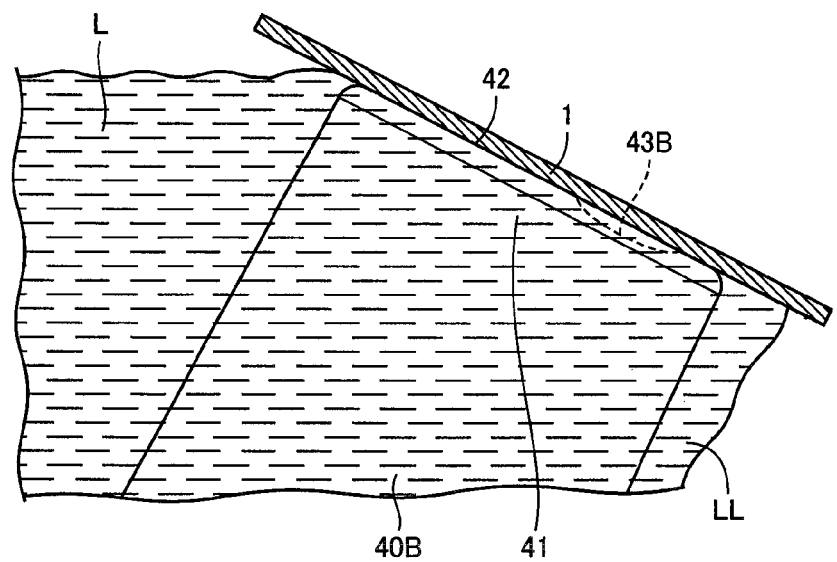
FIG. 22 is a cross sectional view showing a state of a horn oscillator used for a liquid spray apparatus according to a variation of the fifth embodiment at the time of spraying.

Referring to FIG. 22, in the state where the liquid spray apparatus according to the present variation is inclined toward horn oscillator 40, recess 43B may be provided to be positioned at the lower side in the direction of gravity on surface 42 of the leading end 41 of horn oscillator 40. With this structure, liquid L is likely to collect in recess 43B.

Because liquid L is stored in recess 43B, liquid L can be supplied more stably to mesh member 1 without interruption. As a result, liquid L can be sprayed stably.

[Sixth Embodiment]

Figure 23:
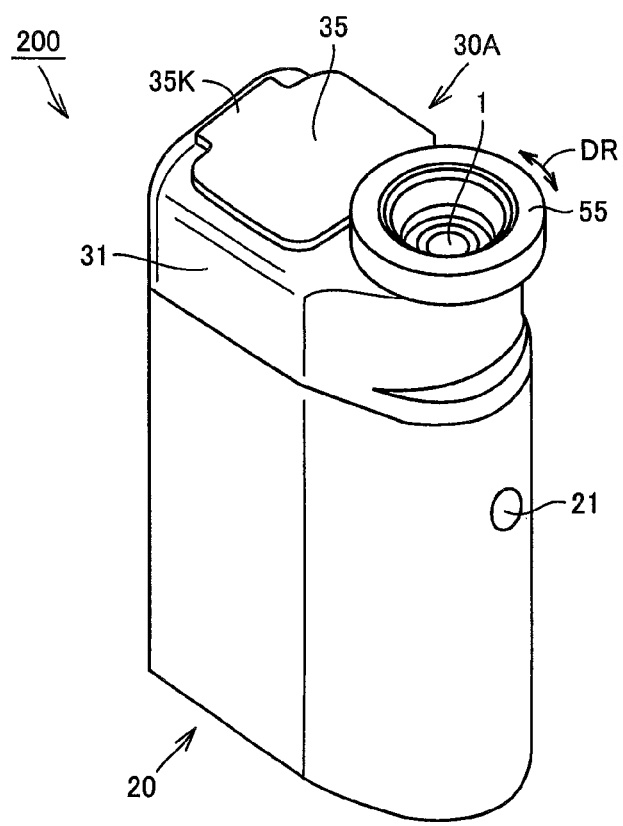
FIG. 23 is a perspective view showing a liquid spray apparatus according to a sixth embodiment.

FIG. 23 is a perspective view showing a liquid spray apparatus 200 according to the present embodiment. Here, a difference from above-described first embodiment will be described. Outer mesh cap 55 in the present embodiment is configured to be detachable from bottle part 31 and is attached to bottle part 31 without being positioned (outer mesh cap 55 is attached at any angle in the direction of arrow DR).

Mesh member 1 held by outer mesh cap 55 becomes rotatable relative to horn oscillator 40, with the state where mesh member 1 and surface 42 (not shown) of leading end 41 (not shown) of horn oscillator 40 (not shown) abut on each other being maintained.

For example, suppose that a user removes outer mesh cap 55 from bottle part 31 together with mesh member 1 and cleans mesh member 1. The user attaches mesh member 1 again to bottle part 31 together with outer mesh cap 55. Outer mesh cap 55 is attached to bottle part 31 without being positioned in the direction of rotation (attached in any phase).

The state in which mesh member 1 is attached onto horn oscillator 40 (not shown) is intended to be changed every time outer mesh cap 55 is attached/detached. With this structure, the orientation in which surface 42 (not shown) of horn oscillator 40 abuts on mesh member 1 is intended to be changed each time. Since the position where mesh member 1 and recess 43 (not shown) abut on each other is intended to be changed each time (concentration of load on mesh member 1 is restrained), the likelihood that mesh member 1 will be damaged can be reduced.

Although the respective embodiments have been described above based on the present invention, the above-described respective embodiments disclosed herein are merely illustration and not restrictive. For example, a plurality of recesses 43, 43A and 43B may be provided. Surface 42 of leading end 41 of horn oscillator 40 may be configured such that a liquid is supplied thereto without inclining liquid spray apparatus 100.

Therefore, the technical scope of the present invention is shown by the appended claims, and is intended to include any modification within the meaning and scope equivalent to the claims.

REFERENCE SIGNS LIST

1 mesh member; 20 body part; 21 power switch; 30 bottle unit; 31 bottle part (liquid storage part); 32 leading end opening; 33 liquid inlet; 35 cap; 35K fixing part; 35T, 38T, 57T support part; 40, 40A, 40B horn oscillator (vibratory source); 41 leading end; 41R processing radius (chamfer dimension); 42 surface; 43, 43A, 43B recess; 43D width; 43H depth; 43*a* first end; 43*b* second end; 43*c* bottom; 50, 52 support member; 51 packing; 55 outer mesh cap; 57 inner mesh cap; 60 opening; 62 inner wall; 100, 200 liquid spray apparatus; AR, DR1, DR2 arrow; B larger capacity section; b smaller capacity section; L, LL liquid; P corner; R edge; S space.

The invention claimed is:

1. A liquid spray apparatus comprising:
    a liquid storage part storing a liquid;
    a vibratory source including a leading end, a recess being formed in a surface of the leading end, wherein the recess intersects perpendicularly to a longitudinal central axis of the vibratory source; and
    a mesh member including a large number of micropores and arranged to abut on the surface of the leading end of the vibratory source, wherein
        the liquid is supplied from the outside of the leading end of the vibratory source to the surface and the recess of the leading end,
        the liquid reaches a lower surface of the mesh member, while flowing from the outside of the leading end into a space created by the recess,
        the liquid supplied to the surface and the recess of the leading end is discharged in an atomized manner through the micropores by a vibration of the vibratory source,
        the recess is formed to extend as a groove and has a first end and a second end facing each other in a direction in which the recess extends, the second end being opposite to the first end, and
        the recess is provided to extend such that the first end reaches an outer circumferential surface of the leading end.

2. The liquid spray apparatus according to claim 1, wherein the recess is provided to extend such that the second end reaches the outer circumferential surface of the leading end.

3. The liquid spray apparatus according to claim 1, wherein the surface of the leading end of the vibratory source is circular, and
    a width of the recess in a direction perpendicular to the direction in which the recess extends is more than or equal to 5% and less than or equal to 50% of a diameter of the surface of the leading end.

4. The liquid spray apparatus according to claim 1, wherein a depth of the recess from the surface of the leading end is more than or equal to 0.03 mm and less than or equal to 1.0 mm.

5. The liquid spray apparatus according to claim 1, wherein the liquid storage part is formed such that, when the liquid spray apparatus is inclined toward the vibratory source, the liquid reaches a neighborhood of a contact part between the leading end of the vibratory source and the mesh member, and such that, when the liquid spray apparatus is held in a horizontal state, the liquid does not reach the neighborhood of the contact part, and
    the recess is provided to extend in the direction in which the liquid spray apparatus is inclined toward the vibratory source.

6. The liquid spray apparatus according to claim 1, wherein an outer edge of the surface of the leading end has been subjected to a chamfering work having a predetermined chamfer dimension, and
    a depth of the recess from the surface of the leading end is smaller than the chamfer dimension.

7. The liquid spray apparatus according to claim 6, wherein the chamfer dimension is larger than 0.1 mm, and
    the depth is 0.1 mm.

8. The liquid spray apparatus according to claim 1, wherein the mesh member is attached to the surface of the leading end of the vibratory source in an inclined manner at a predetermined angle (θ1).

9. The liquid spray apparatus according to claim 8, wherein, in a projection in which the mesh member is projected toward the leading end of the vibratory source, the mesh member is attached to the leading end of the vibratory source such that a direction in which the mesh member is inclined and the direction in which the recess extends intersect with each other.

10. The liquid spray apparatus according to claim 1, wherein the mesh member is configured to be rotatable relative to the vibratory source while a state in which the mesh member and the surface of the leading end of the vibratory source abut on each other is maintained.

11. The liquid spray apparatus according to claim 1, wherein a surface roughness of a bottom of the recess is formed more roughly than the surface roughness of the surface.

* * * * *